United States Patent [19]

Gerace

[11] Patent Number: 5,311,366
[45] Date of Patent: May 10, 1994

[54] MIRROR ADAPTED FOR USE IN SELF-CATHETERIZING PROCEDURES

[75] Inventor: Joseph A. Gerace, Nokomis, Fla.

[73] Assignee: Paul A. Hostetler, Sarasota, Fla.

[21] Appl. No.: 6,539

[22] Filed: Jan. 21, 1993

[51] Int. Cl.$^5$ ............................................. G02B 7/182
[52] U.S. Cl. .................................. 359/879; 359/872;
248/476; 128/22; 128/3; 128/18; 362/138;
362/139; 362/103; 602/24
[58] Field of Search ................ 359/872, 879; 248/476,
248/480, 276, 298, 200.1; 128/3, 21, 22, 17, 18;
602/24, 25; 362/103, 138, 139

[56] References Cited

U.S. PATENT DOCUMENTS

| | | |
|---|---|---|
| 1,183,747 | 5/1916 | McIntire . |
| 1,389,053 | 8/1921 | King . |
| 1,439,836 | 12/1922 | Pease . |
| 1,681,874 | 8/1928 | Ouellet . |
| 2,312,608 | 3/1943 | Wadsack . |
| 3,228,399 | 1/1966 | Riedell . |
| 3,411,842 | 11/1968 | Levy . |
| 4,257,680 | 3/1981 | Baczkowski . |
| 4,576,151 | 3/1986 | Carmichael et al. ................ 602/24 |
| 4,623,955 | 11/1986 | Santini ................................ 128/22 |

OTHER PUBLICATIONS

"Richards PEHR Abduction Hip Splint", Journal of Bone & Joint Surgery, Mar. 1965, vol. 47-A, p. 81.

Primary Examiner—Edward K. Look
Assistant Examiner—James A. Larson
Attorney, Agent, or Firm—Burns, Doane, Swecker & Mathis

[57] ABSTRACT

A personal hygiene mirror assembly is mountable on a sitting person's legs to enable the person to view the anal or genital area while leaving the person's hands free to perform a personal hygiene procedure. The mirror assembly includes a mirror which can be adjusted to a plurality of inclinations. The mirror assembly is mounted on the person's legs by means of leg grips which are slidable with the person's legs when the legs are spread apart or brought together. Such movement of the legs can be made without changing the selected inclination of the mirror.

16 Claims, 3 Drawing Sheets

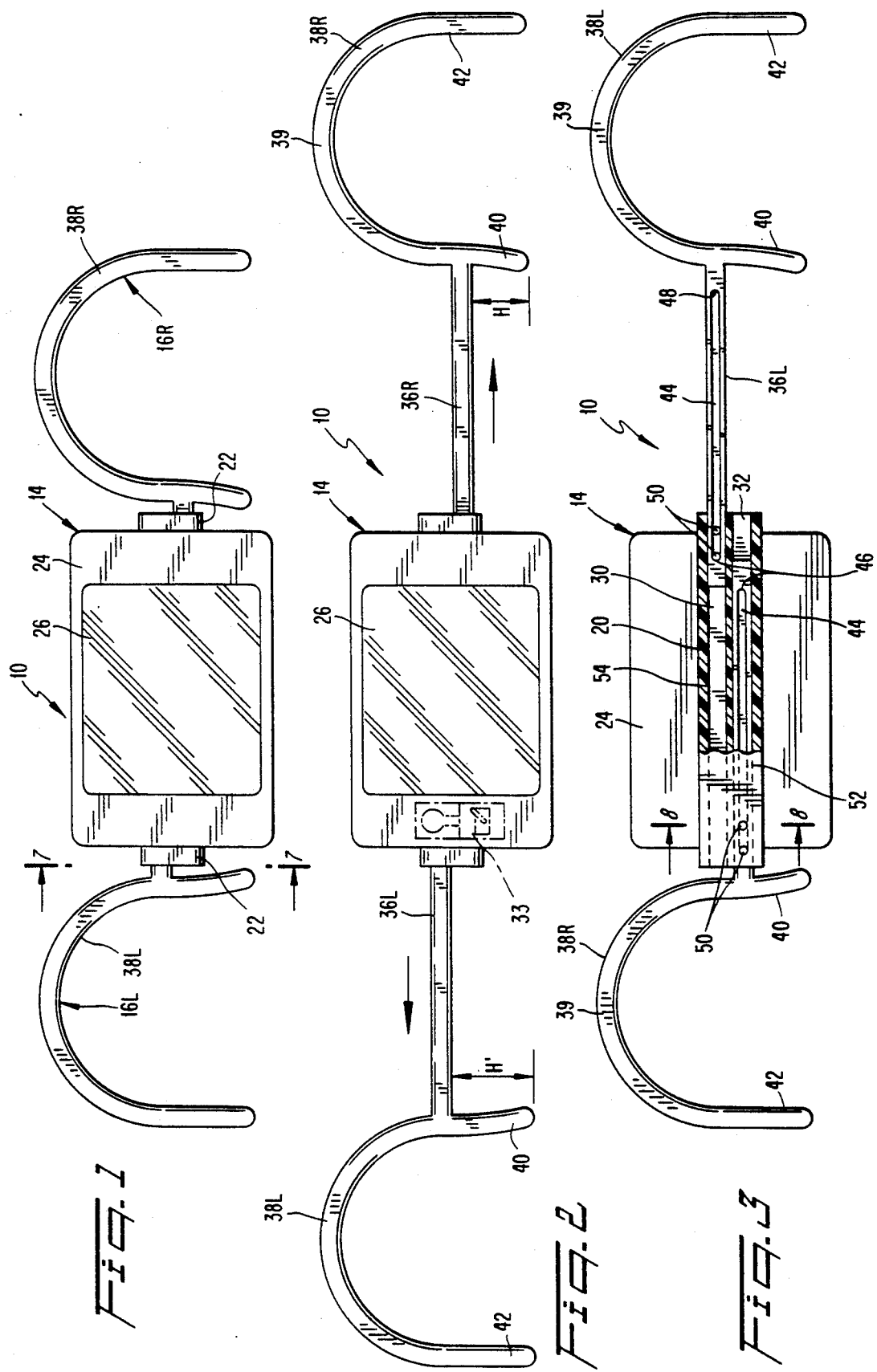

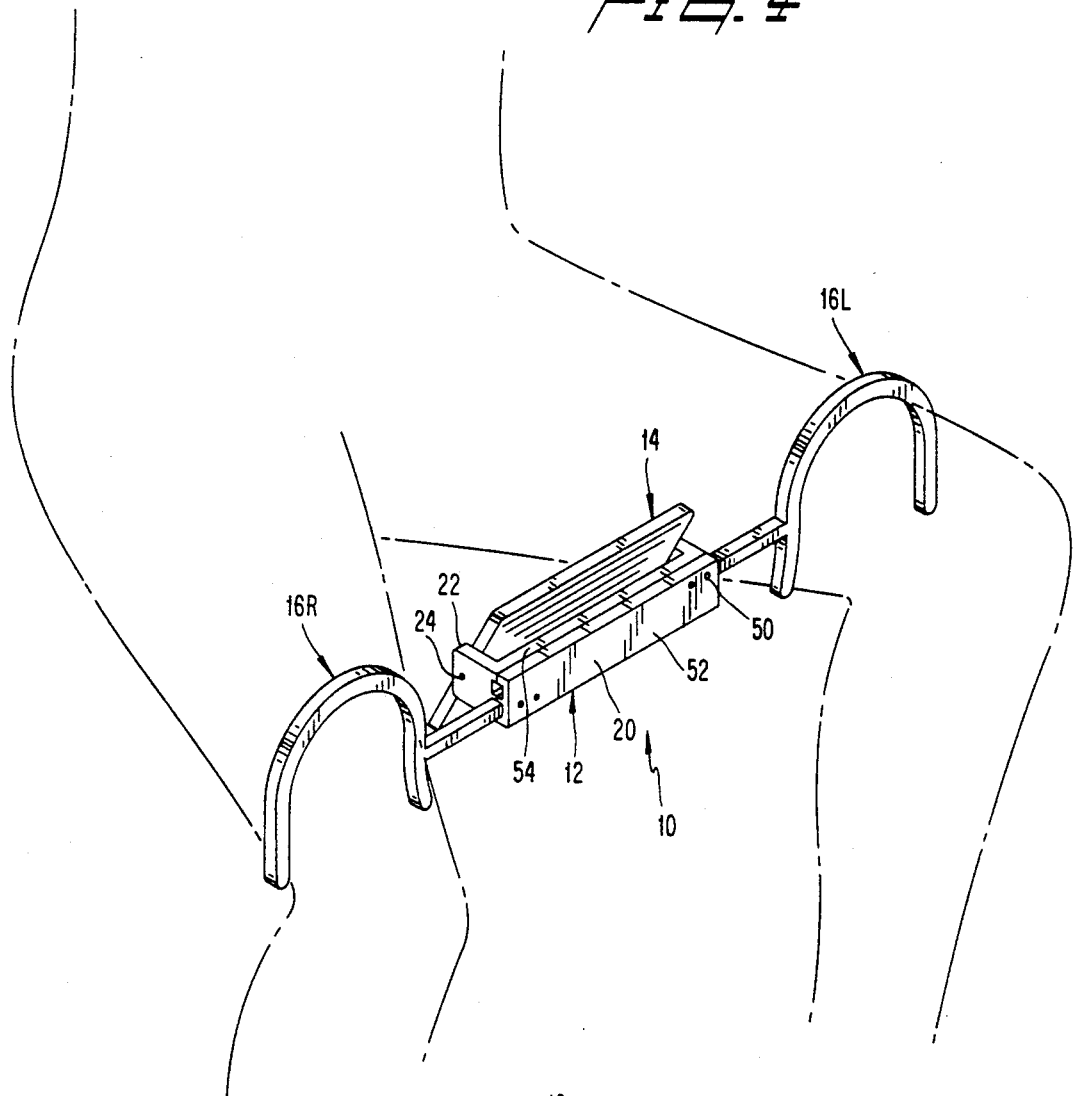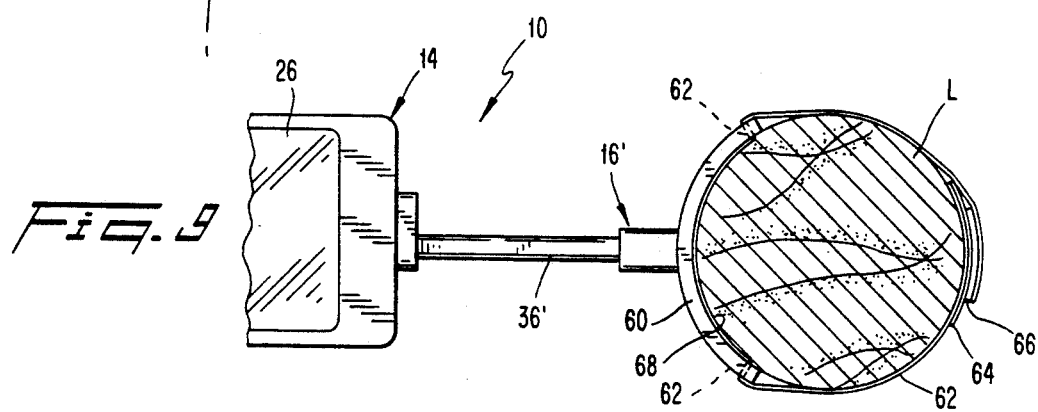

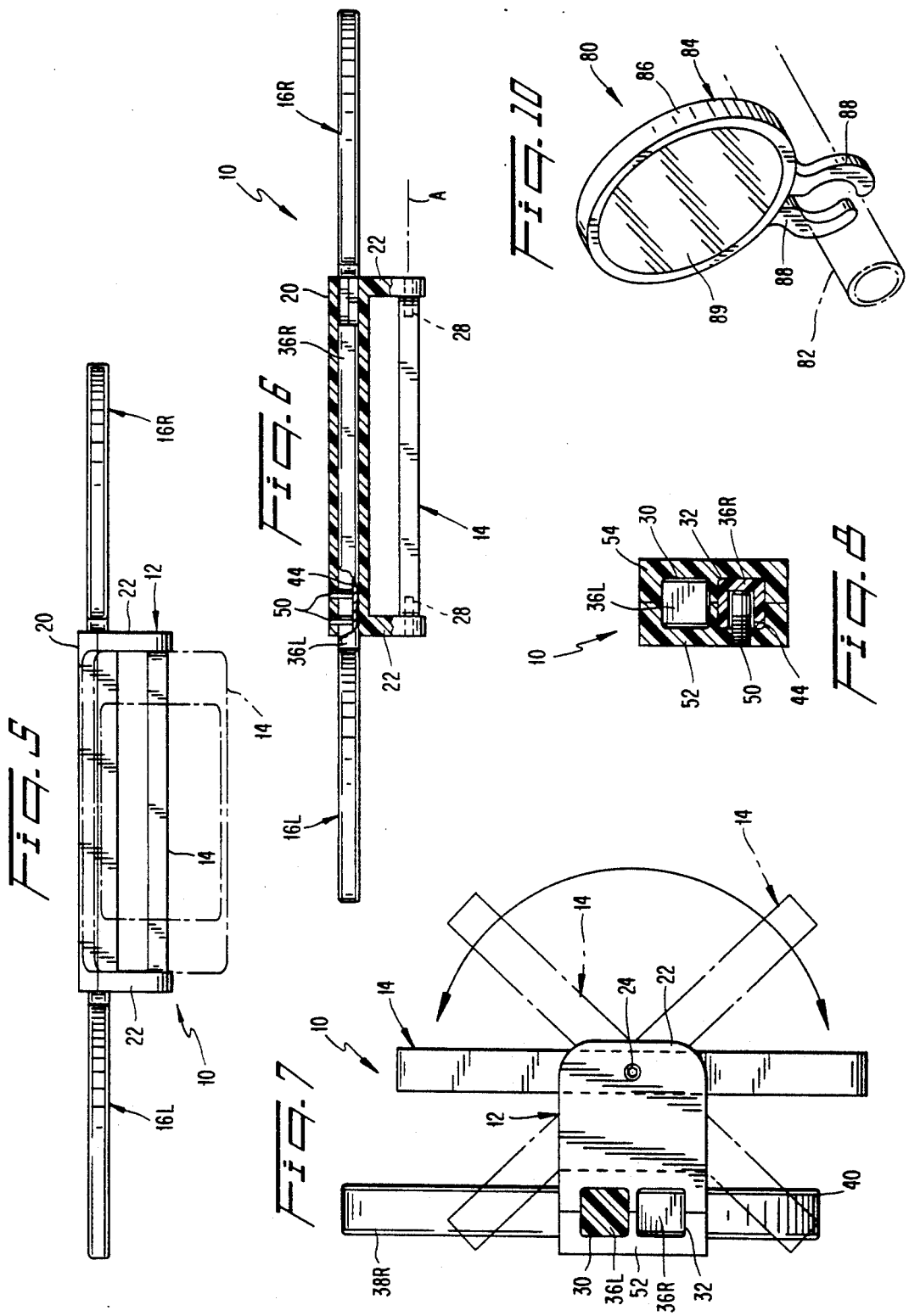

MIRROR ADAPTED FOR USE IN SELF-CATHETERIZING PROCEDURES

BACKGROUND OF THE INVENTION

The present invention relates to a personal hygiene mirror that can be held between a user's legs.

It may become necessary for a person to perform personal hygiene procedures in the area of his or her genital or anal areas, e.g., the installation of tampons, suppositories, catheters and birth control devices such as sponges and diaphragms, as well as self examination procedures to aid in the early detection and treatment of hemorrhoids, cysts, tumors, genital rashes, fissures, etc.

It may be difficult to perform the procedure without the use of a mirror. However, since the person's hands will be occupied in performing the hygiene procedure, the person cannot hold the mirror.

For example, females with a neurogenic bladder condition to perform a self-catheterizing procedure wherein a catheter tube is inserted into the vagina to cause urine to flow. This procedure requires the use of a mirror and is very difficult to accomplish with one hand holding the mirror.

There have previously been proposed mirrors which are able to be held by a person's leg or legs. One such mirror, disclosed in Baczkowski U.S. Pat. No. 4,257,680, can be strapped to one leg of a person. It will be appreciated that such a mirror is not ideally suited for viewing the genital or anal area, especially if the procedure being performed requires the person to spread his or her legs far apart. That is, when the legs are spaced apart, the mirror is carried away from the genital or crotch area.

There is disclosed in Levy U.S. Pat. No. 3,411,842 a personal hygiene mirror assembly which leaves a person's hands free to shave or apply facial make-up. That mirror assembly includes a mirror which is mounted between a pair of clamps. The assembly is adapted to be held between a person's legs by moving the legs toward one another and against the horizontally open sides of the clamps. The clamps are spring-biased outwardly to keep the clamps pressed against the person's legs and also to enable the inclination of the mirror to be adjusted about a horizontal axis. That is, by pressing the clamps toward one another, a motion transfer linkage connected between the clamps and mirror, causes the mirror to be pivoted about the horizontal axis so that the user can direct the mirror toward the person's face. Such a mirror assembly is not ideally suited as a personal hygiene mirror for viewing a person's anal or genital area, because of the inability to maintain the mirror inclination while spreading the legs apart. The assembly is designed such that the person must position his or her legs relatively close together, and only little movement of the legs thereafter is possible; if the person spreads the legs too far apart, the assembly would fall off the legs.

SUMMARY OF THE INVENTION

The present invention relates to a personal hygiene mirror assembly comprising a base, a mirror mounted on the base, and a pair of leg grips connected to the base. The leg grips enable the assembly to be mounted to the legs of a sitting person with the mirror centered between the person's legs. The leg grips are configured such that the person's legs pull the leg grips out as the legs are spread apart, or push the leg grips in as the legs are brought together.

Preferably, the mirror is adjustable to a plurality of inclinations. The leg grips are horizontally extensible and retractable relative to the base without altering the inclination of the mirror.

Another aspect of the invention involves a mirror adapted to be removably inserted on an elongated member. The mirror comprises a frame bordering a reflective surface, and a pair of flexible fingers projecting from a peripheral edge of the frame. The fingers are spreadable for attachment to the outside of the elongated member. Such a mirror is useful in a method of inserting a catheter tube into a person's body cavity. The mirror would be attached to the catheter tube to enable the person to view the body cavity while leaving the person's hands free to manipulate the tube.

BRIEF DESCRIPTION OF THE DRAWINGS

The objects and advantages of the invention will become apparent from the following detailed description of preferred embodiments thereof in connection with the accompanying drawings in which like numerals designate like elements, and in which:

FIG. 1 is a front elevational view of a personal hygiene mirror assembly according to the present invention, with the leg grips pushed fully inwardly;

FIG. 2 is a view similar to FIG. 1, after the leg grips have been displaced fully outwardly;

FIG. 3 is a rear elevational view of the mirror assembly, with a portion thereof broken away;

FIG. 4 is a perspective view of the mirror assembly in use;

FIG. 5 is a top plan view of the mirror assembly;

FIG. 6 is a view similar to FIG. 5, with a base portion of the assembly broken away;

FIG. 7 is a sectional view taken along the line 7—7 in FIG. 1;

FIG. 8 is a cross-sectional view of a rear wall the base, taken along the line 8—8 in FIG. 3;

FIG. 9 is a fragmentary front elevational view of a personal hygiene mirror depicting an alternative way of attaching the mirror to a user's legs; and FIG. 10 is a perspective view of a different form of mirror according to the present invention.

DETAILED DESCRIPTION OF PREFERRED EMBODIMENTS OF THE INVENTION

A personal hygiene mirror assembly 10 comprises a base 12, a mirror 14 mounted to the base 12, and a pair of leg grips 16R, 16L projecting in opposite directions from the base. The base 12 is U-shaped and includes a bight portion 20 and a pair of parallel arms 22 projecting forwardly from opposite ends of the bight portion.

The mirror 14 comprises a frame 24 carrying a reflective surface 26, e.g., glass or plastic. The mirror could be fixed stationarily to the base, but preferably the frame 24 is mounted to and between the ears 22 for rotation about a horizontal axis A (see FIG. 6) by means of a pair of pivot pins 28. Consequently, the mirror can be rotated to various positions of adjustment as shown in broken lines in FIG. 7. The mirror is held in the various positions of adjustment by any suitable expedient, such as a friction fit between the frame 24 and the arms 22 as shown, or alternatively by a detent (not shown) projecting laterally outwardly from each side of the frame which enters different ones of spaced recesses in the arms as the mirror is rotated. Other types of holding means will be apparent to those skilled in the art.

The bight portion 20 includes a pair of horizonal slots 30, 32 extending parallel to the axis A. The slots 30, 32 are vertically spaced whereby the slots constitute upper and lower slots 30, 32 (see FIG. 3).

Each of the leg grips 16R, 16L includes a horizontal post 36R, 36L and a downwardly open U-shaped gripping portion 38R, 38L. The posts 36R, 36L are slidably mounted in respective slots 30, 32. Each gripping portion 38R, 38L includes a top 39 and a pair of horizontally spaced downwardly extending inner and outer fingers 40, 42. Each post 36R, 36L is of integral one-piece construction with a respective inner finger 40, and a groove 44 extends lengthwise along the post. The groove has terminal end surfaces 46, 48. Two pairs of stop pins 50 are mounted in the bight portion 20 of the base and extend across the slots 30, 32 so as to project into the grooves 44. An inner pin of each pair of pins 50 serves as a stop to limit the extent to which a respective post can be pulled laterally outwardly, as shown in FIG. 3.

The post 36R is attached to the inner finger 40 of its respective gripping portion at a height H which is shorter than the height H, at which the other post 36L is attached to its respective finger 40.

The bight portion 20 of the base 12 may be formed in two parts 52, 54 for ease of manufacture. Each of the parts 52, 54 forms one half of each slot 30, 32, and the parts are fixedly secured together, e.g., by adhesive, screws, welding, etc.

If desired, a lamp could be attached to the assembly, e.g., a battery powered lamp 33 mounted on a side of the frame 24 as shown in phantom lines in FIG. 2. Alternatively, the lamp could be mounted elsewhere, e.g., along a top or bottom of the frame. Such a lamp would illuminate the body area being inspected.

As an alternative to the inverted U-shaped leg grips 16R, 16L previously discussed, it may be preferable to employ leg grips 16' having a Velcro ® strap arrangement (see FIG. 9). Such a leg grip 16, includes a post 36' to which is attached an arch-shaped support 60 made of stiff plastic for example. At each end of the support 60 there is provided a through-slot 62. Extending through the through-slots is a flexible strap 62. Velcro fastening elements 64, 66 are mounted to the strap 62 adjacent respective ends thereof. One element 64 faces outwardly, and the other element 66 faces inwardly. In use, one section 68 of the strap 62 extends along a surface of the support 60 and becomes sandwiched between that surface and an inner side of a user's leg L when the support 60 is pushed thereagainst. The ends of the strap are then wrapped around the user's legs, and the velcro fastening elements 64, 66 are fastened together. Hence, the leg grips 16' are constrained to move outwardly and inwardly together with the user's legs.

In use, the person assumes a sitting position and mounts the assembly 10 on his or her legs by pressing the U-shaped gripping portions 38R, 38L downwardly upon the legs at a location above the knee as shown in FIG. 4. This is done with the mirror 14 facing the person's anal or genital area. The mirror 14 is then adjusted to a desired inclination by rotating the mirror about the axis A. The legs of the person can be freely opened and closed without changing the inclination of the mirror 14. Since each gripping portion 38R, 38L has horizontally spaced fingers 40, 42, the leg grips 16R, 16L can be pulled outwardly along with the person's legs. The tops 39 of the gripping portions extend over the tops of the person's legs to prevent the assembly from falling off. Hence, the person can adjust his or her legs to any desired spacing while maintaining the pre-set inclination of the mirror. The person's hands are thus free to perform the necessary hygiene procedure, such as a self-catheterizing procedure, in the anal or genital area while being able to view the procedure via the mirror which remains centered between the legs. The inclination of the mirror can be changed at any time without moving the legs.

The mirror assembly can be formed primarily of light-weight plastic so as to minimize its over-all weight.

Another aspect of the present invention, depicted in FIG. 10, involves a mirror 80 which can be removably attached to a catheter tube 82 that is being inserted into a body cavity, e.g., for draining fluid in the vaginal area. That mirror 80 comprises a frame 84 having a circular portion 86 and a pair of clamp fingers 88 projecting out from a peripheral edge of the circular portion 86. That circular portion borders a reflective surface 89. The fingers 88 are flexible (e.g., formed of plastic) and are generally curved so as to be able to snap onto the catheter tube 82 when pushed thereagainst. The mirror enables the body area to be viewed while leaving the person's hands free to manipulate the tube. As the tube is inserted, the mirror can be slid longitudinally along the tube, since it is secured longitudinally by a friction fit.

Although the invention has been described in connection with preferred embodiments thereof, it will be appreciated by those skilled in the art that additions, modifications, substitutions, and deletions not specifically described may be made without departing from the spirit and scope of the invention as defined in the appended claims.

What is claimed is:

1. A personal hygiene mirror assembly comprising:
    a base;
    a mirror mounted on said base; and
    a pair of leg grips connected to said base for mounting said assembly to the legs of a sitting person with said mirror centered between the person's legs, said leg grips being movable inwardly and outwardly relative to said base and including mounting means for mounting said leg grips to the person's legs such that the person's legs pull said leg grips outwardly relative to said base when the person's legs are spread apart, and push the leg grips inwardly relative to said base when the person's legs are brought together.

2. A personal hygiene mirror assembly according to claim 1, wherein said mirror is mounted for adjustment to a plurality of inclinations, said leg grips being arranged for said inward and outward movement relative to said base without altering the inclination of said mirror.

3. A personal hygiene mirror assembly according to claim 1, wherein said mounting means for each grip includes a downwardly open U-shaped portion insertable downwardly onto one of the legs of the person.

4. A personal hygiene mirror assembly according to claim 3, wherein each of said leg grips includes a post slidable horizontally within said base, said U-shaped portions being situated at outer ends of respective posts.

5. A personal hygiene mirror assembly according to claim 4 including stop means limiting the extent to which said leg grips can be slid outwardly relative to said base.

6. A personal hygiene mirror assembly according to claim 4, wherein said posts are slidable in respective horizontal slots formed in said base, said slots being disposed parallel to one another.

7. A personal hygiene mirror assembly according to claim 6, wherein said slots are disposed one above the other.

8. A personal hygiene mirror assembly according to claim 4, wherein said mirror is rotatable about a horizontal axis for adjusting its inclination, said axis being parallel to said posts.

9. A personal hygiene mirror assembly according to claim 8, wherein said base is U-shaped and includes a bight portion and two parallel arms, said mirror being rotatably mounted to and between said arms, said posts being mounted in said bight portion.

10. A personal hygiene mirror assembly according to claim 1, wherein said mounting means comprises a velcro strap arrangement.

11. A personal hygiene mirror assembly according to claim 1, wherein each of said leg grips includes a post slidable horizontally within said base.

12. A personal hygiene mirror assembly according to claim 1, wherein said mirror is rotatable about a horizontal axis for adjusting its inclination.

13. A personal hygiene mirror assembly according to claim 1 including an electric lamp mounted on said assembly.

14. A personal hygiene mirror assembly according to claim 13, wherein said lamp is mounted on said mirror.

15. A personal hygiene mirror assembly according to claim 14, wherein said lamp is a battery-powered lamp.

16. A personal hygiene mirror assembly comprising:
a base having a pair of parallel horizontal slots;
a mirror mounted to said base for rotation relative thereto about a horizonal axis for adjustment between a plurality of inclinations;
a pair of leg grips connected to said base for mounting said assembly to a sitting person's legs with said mirror centered between the person's legs, each of said leg grips including:
a post slidable within a respective one of said slots, and
a downwardly open U-shaped portion disposed at an outer end of said post for being installed onto a sitting person's legs at a location above the knees; and
said leg grips being pulled out and pushed in relative to said base when the person's legs are spread apart and brought together, respectively, without changing the inclination of said mirror.

* * * * *